(12) United States Patent
Furbush, Jr.

(10) Patent No.: US 9,084,558 B2
(45) Date of Patent: Jul. 21, 2015

(54) ANGULAR ROTATION GUIDANCE DEVICE FOR A SURGICAL INSTRUMENT

(75) Inventor: Norman C. Furbush, Jr., Elm City, NC (US)

(73) Assignee: Syntervention, Inc., Rocky Mount, NC (US)

( * ) Notice: Subject to any disclaimer, the term of this patent is extended or adjusted under 35 U.S.C. 154(b) by 513 days.

(21) Appl. No.: 13/367,200

(22) Filed: Feb. 6, 2012

(65) Prior Publication Data

US 2012/0199060 A1    Aug. 9, 2012

Related U.S. Application Data

(60) Provisional application No. 61/440,142, filed on Feb. 7, 2011.

(51) Int. Cl.

| A61B 5/06 | (2006.01) |
|---|---|
| A61B 6/12 | (2006.01) |
| A61M 25/01 | (2006.01) |
| A61M 25/09 | (2006.01) |
| A61B 19/00 | (2006.01) |
| A61B 17/00 | (2006.01) |
| A61M 25/00 | (2006.01) |

(52) U.S. Cl.
CPC .............. *A61B 5/065* (2013.01); *A61B 19/46* (2013.01); *A61M 25/0105* (2013.01); *A61M 25/09041* (2013.01); *A61B 5/066* (2013.01); *A61B 6/12* (2013.01); *A61B 2017/00455* (2013.01); *A61B 2017/00469* (2013.01); *A61B 2019/467* (2013.01); *A61M 2025/0008* (2013.01)

(58) Field of Classification Search
CPC .......... A61B 5/065; A61B 5/066; A61B 6/12; A61B 19/46; A61B 2017/00455; A61B 2017/00464; A61B 2017/00469; A61B 2019/467; A61B 2019/468; A61B 2019/469; A61M 25/0105; A61M 25/09041; A61M 2025/0008
USPC .......... 116/200, 201, 309, 319, 320; 33/1 LE, 33/334, 335, 347, 365, 368, 369, 371, 377, 33/379, 389, 391, 396, 399, 512, DIG. 26; 604/116, 264; 606/130
See application file for complete search history.

(56) References Cited

U.S. PATENT DOCUMENTS

| 1,451,507 | A |   | 4/1923 | Harris et al. |
|---|---|---|---|---|
| 3,707,772 | A | * | 1/1973 | Cotter ............................. 33/373 |
| 4,479,800 | A | * | 10/1984 | Chester ......................... 604/187 |
| 4,602,645 | A |   | 7/1986 | Barrington et al. |
| 4,733,661 | A | * | 3/1988 | Palestrant ..................... 606/108 |
| 5,005,592 | A |   | 4/1991 | Cartmell |
| 5,102,391 | A | * | 4/1992 | Palestrant ..................... 604/116 |
| 5,196,019 | A | * | 3/1993 | Davis et al. ................... 606/130 |
| 5,201,742 | A | * | 4/1993 | Hasson .......................... 606/130 |

(Continued)

FOREIGN PATENT DOCUMENTS

WO    WO 87/02883 A1    5/1987

*Primary Examiner* — R. A. Smith
(74) *Attorney, Agent, or Firm* — Aspire IP, LLC; Scott J. Hawranek

(57) ABSTRACT

A guidance device for determining the angular orientation of the distal end of a surgical instrument, comprising an indicator portion containing a constant vertical reference attached to a securing portion for attaching to the surgical instrument shaft. The guidance device has graduated markings upon it for indicating angle of surgical instrument rotation from the vertical reference.

20 Claims, 7 Drawing Sheets

(56) References Cited

U.S. PATENT DOCUMENTS

| | | | |
|---|---|---|---|
| 5,228,441 A * | 7/1993 | Lundquist | 600/380 |
| 5,322,064 A * | 6/1994 | Lundquist | 600/381 |
| 5,449,346 A * | 9/1995 | Buffington et al. | 604/115 |
| 5,545,200 A | 8/1996 | West et al. | |
| 5,728,178 A * | 3/1998 | Buffington et al. | 604/115 |
| 5,954,670 A * | 9/1999 | Baker | 600/567 |
| 6,073,356 A * | 6/2000 | Li | 33/391 |
| 6,468,166 B1 | 10/2002 | Spitzer | |
| 6,638,281 B2 * | 10/2003 | Gorek | 606/96 |
| D490,004 S | 5/2004 | Koshino | |
| 6,989,015 B2 * | 1/2006 | Daum et al. | 606/130 |
| 7,302,288 B1 | 11/2007 | Schellenberg | |
| 7,484,305 B2 | 2/2009 | Sherry et al. | |
| 7,775,899 B1 | 8/2010 | Cannon | |
| 2004/0133185 A1* | 7/2004 | Nash et al. | 604/533 |
| 2005/0033315 A1* | 2/2005 | Hankins | 606/129 |
| 2006/0025778 A1* | 2/2006 | Ferree | 606/102 |
| 2007/0149878 A1* | 6/2007 | Hankins | 600/427 |
| 2010/0013655 A1* | 1/2010 | Lopera | 340/686.1 |
| 2010/0087823 A1* | 4/2010 | Kondrashov | 606/79 |
| 2010/0280354 A1* | 11/2010 | Zhang et al. | 600/411 |

* cited by examiner

ANGULAR ROTATION GUIDANCE DEVICE FOR A SURGICAL INSTRUMENT

This application claims the benefit of U.S. Provisional Patent Application No. 61/440,142, filed on Feb. 7, 2011, which is hereby incorporated by reference for all purposes as if fully set forth herein.

BACKGROUND OF THE INVENTION

1. Field of the Invention

The present invention generally relates to guidance devices and more particularly to angular rotation guidance devices for surgical instruments.

2. Discussion of the Related Art

Guidewires and catheters are used in a variety of different medical procedures, for example, during angiographic, endovascular, or other surgical procedures. Guidewires are typically used to position catheters in a body lumen, for example arteries, veins or natural orifices within a mammal. The leading end portion (distal end) of the guidewire is typically introduced into the body through an incision or natural orifice and then advanced to the treatment area. To reach the treatment area, the guidewire may have to be steered into lumens bifurcating from the body lumen. To ensure the guide wire moves into the desired lumen, the distal end of the wire is bent at an angle or into a "J" shape, and the trailing (proximal) end of the wire outside the body is rotated to position the guide wires distal end into the correct lumen to reach the treatment area.

Typically, this is accomplished under x-ray guidance as the distal segment of the guidewire is visible. For example, a radiopaque marker is on the device and under x-ray and/or contrast various aspects and locations of the device may be visualized. Similarly, many catheters have shaped distal ends to allow them to be rotated and steered to various locations in the body. Some catheters are meant to be used over a guidewire and have distal ends which are mounted eccentric to the guidewire. These catheters are rotated from the proximal end to move the eccentric distal tip to one side of the body lumen to deliver treatment.

Advancing and steering surgical instruments in the body under fluoroscopic guidance can be rather difficult as the visual image provided is 2-dimensional and the body lumen anatomy and surgical instrument are working in 3 dimensions. For example, when a J-tipped guidewire is rotated in a lumen, the direction and angular orientation of the J-tip is easily seen when the plane of the "J" is perpendicular to the vector defined by the line of the x-ray source to the patient. As the wire is rotated away from this perpendicular plane, it becomes difficult to determine where the J-tip is pointed. When the plane of the "J" is parallel to the source vector, the "J" shape appears as a single line on the x-ray screen, and it is difficult, if not impossible to discern if the "J" is pointed toward or away from the x-ray source. If the plane of the "J" is at 45 degrees or 135 degrees to the source vector, it will appear as the same image on the x-ray screen. Difficulty in determining the angular orientation of the distal end of the surgical instrument may lead to extended procedure times, suboptimal treatment, and in extreme cases, complications and/or failed treatment.

Therefore, a device and method for determining the angular orientation of surgical instruments within the body is desired.

SUMMARY OF THE INVENTION

Accordingly, this invention is directed to an angular rotation guidance device for a surgical instrument that substantially obviates one or more of the problems due to limitations and disadvantages of the related art.

An advantage of the invention is to provide a device to accurately measure and display the angular rotation of a surgical instrument within the body.

Another advantage of the invention is to provide a mechanism to attach the angular rotation measurement device to a surgical instrument for purposes of accurately measuring angular rotation.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an aspect of the invention is directed towards a guidance device for determining the angular orientation of the distal end of a surgical instrument. The guidance device includes an indicator portion containing a constant vertical reference attached to a securing portion for attaching to the surgical instrument, e.g., a shaft of a surgical instrument. The guidance device may include graduated markings upon it for indicating the angle of the surgical instrument rotation from the vertical reference.

The indicator portion may be orientated such that it is substantially coaxial to the surgical instrument shaft. In one embodiment, the guidance device has graduated markings upon it for indicating direction of the surgical instrument rotation from the vertical reference.

Another aspect of the invention is directed towards an angular rotation guidance device configured to use with a surgical instrument. The angular rotation guidance device includes an indicator and a securing device coupled to the indicator. The indicator is configured to provide 360 degrees of angular rotational measurement of the surgical instrument.

Yet another aspect of the invention is directed towards an angular rotation guidance apparatus configured for use with a surgical instrument. The device includes an indicator which has a constant vertical reference and a hub coupled to the indicator. The indicator is configured to provide angular rotational measurement of the surgical instrument and the hub is configured to couple the surgical instrument to the device in a coaxial orientation.

Still yet another aspect of the invention is directed towards a method of using a guidance device to provide an angular orientation of a distal end of a surgical instrument. The method includes attaching a guidance device to the surgical instrument, aligning the guidance device and an indicator to the orientation of the surgical instrument and measuring a degree of rotation of a portion of the surgical device with the indicator.

Yet another aspect of the invention is directed towards a kit. The kit includes a surgical instrument and an angular rotation guidance device according to an embodiment of the invention. The guidance device includes an indicator and a securing mechanism coupled to the indicator. The indicator is configured to provide 360 degrees of angular rotational measurement of the surgical instrument. The kit also optionally includes instructions for use.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention, are incorporated in and constitute a part of this specification. They illustrate embodiments of the invention and together with the description serve to explain the principles of the invention.

In the drawings.

DETAILED DESCRIPTION OF THE ILLUSTRATED EMBODIMENTS

Figure 1:
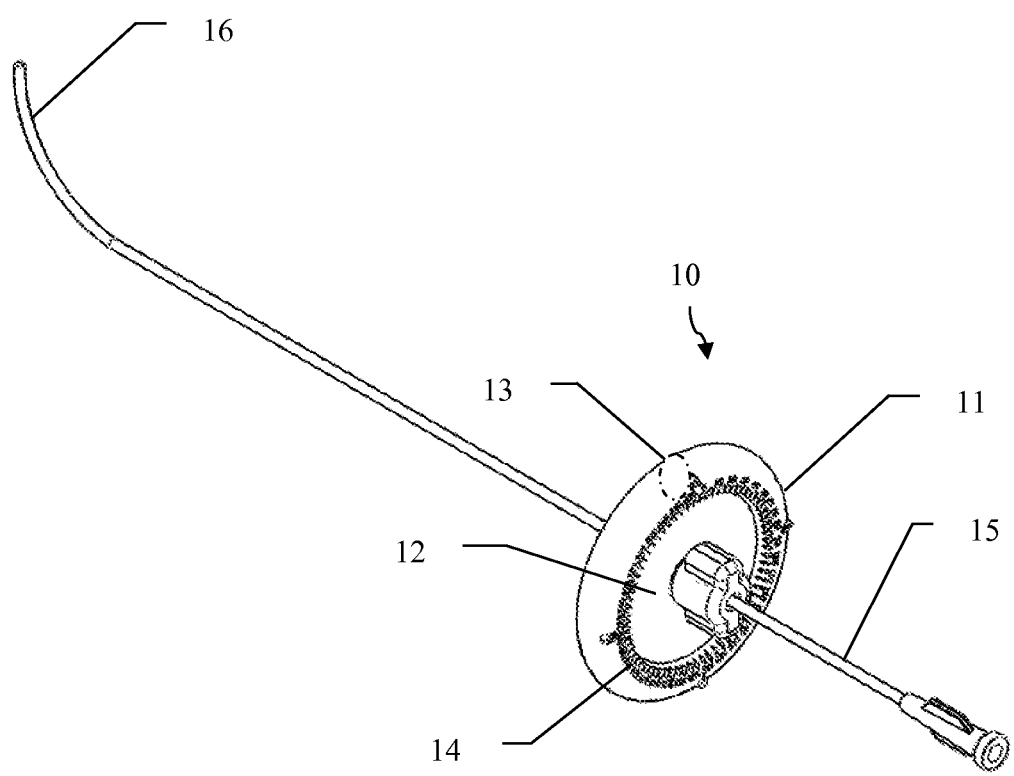
FIG. 1 is a perspective view of the guidance device according to an embodiment of the invention.

The invention relates to a guidance device and more particularly to an angular rotation guidance device for use with one or more surgical instruments. The expression "surgical instrument(s)" will be used herein to include all kinds of elongated members used during medical procedures, in particular a catheter, guidewire, needle, forceps, biotome, endoscope, laparoscope, trocar and/or combinations of the same.

In another embodiment, the angular rotation guidance device includes an indicator and a securing device coupled to the indicator. The indicator is configured to provide 360 degrees of angular rotational measurement of the surgical instrument. The indicator portion may be orientated such that it is substantially coaxial to the surgical instrument shaft. The guidance device includes graduated markings upon it for indicating direction of the surgical instrument rotation from the vertical reference.

In yet another embodiment, the device is directed towards an angular rotation guidance apparatus for use with a surgical instrument. The device includes an indicator which has a constant vertical reference and a hub coupled to the indicator. The indicator is configured to provide angular rotational measurement of the surgical instrument and the hub is configured to couple the surgical instrument to the device in a coaxial orientation.

The constant vertical reference may include any mechanism configured to provide a reference at a vertical most point of the indicator, e.g., 12 o'clock position, to provide a constant vertical reference point during rotation of the surgical instrument. For example, the constant vertical reference may include at least one spirit level including a gas bubble and a fluid. The fluid may include an alcohol solution and may be colored with various pigments, e.g., fluorescent material to provide enhanced readability. In another embodiment, the constant vertical reference may include a pointer and a counter weight as described herein.

In still another embodiment, the invention is directed towards a method of using a guidance device to provide an angular orientation of a distal end of a surgical instrument as provided. The method includes attaching a guidance device to the surgical instrument, aligning the guidance device and an indicator to the orientation of the surgical instrument and measuring a degree of rotation of a portion of the surgical device with the indicator.

In yet another embodiment, the invention is directed towards a kit. The kit includes a surgical instrument and an angular rotation guidance device for use with a surgical instrument. The device includes an indicator and a securing device coupled to the indicator. The indicator is configured to provide 360 degrees of angular rotational measurement of the surgical instrument. The kit also optionally includes instructions for use.

In still another embodiment, the guidance device is utilized with an electrophysicology (EP) catheter as described with reference to U.S. Pat. No. 5,545,200, which is hereby incorporated by reference as if fully set forth herein. That is, the device is configured to provide an angular rotation measurement of the deflected tip of the EP catheter.

In yet another embodiment, the indicator portion is coaxial to the surgical instrument shaft.

In still another embodiment, the guidance device has graduated markings upon it for indicating direction of surgical instrument rotation from the vertical reference.

In another embodiment, the indicator portion is a circular spirit level and the vertical reference is a gas bubble.

In yet another embodiment, the vertical reference is a pointer with attached counter-weight.

In still another embodiment, the securing portion contains a Touhy Borst adapter.

In yet another embodiment, the vertical reference is a counter-weight.

In another embodiment, the indicator portion includes a single circular spirit level mounted on the securing portion. The spirit level is configured to extend around the catheter shaft less than 360 degrees.

In yet another embodiment, the indicator portion consists of 2 semi circular spirit levels mounted on the securing portion.

In still another embodiment, the guidance device has features to permit side loading onto the surgical instrument shaft.

In yet another embodiment, the indicator portion is a helical shaped spirit level.

In still yet another embodiment, the indicator is configured as a handle or incorporated into the surgical device as a handle. For example, a circumferential portion or other portion of the indicator may be used as a handle to aid in rotating the surgical instrument. Of course, any portion of the device could also be used as a handle to rotate the catheter, or alternatively, the guidance device is built into an existing handle for rotating a catheter.

Reference will now be made in detail to an embodiment of the present invention, an example of which is illustrated in the accompanying drawings.

FIG. 1 shows a guidance device 10 according to an embodiment of the invention to determine the angular rotation of surgical instruments. In various embodiments as shown in the drawings, the guidance device 10 is generally a circular shaped indicator portion 11 attached to a securing portion 12.

Securing portion 12 contains a mechanism for attaching a device to the surgical instrument 15. The indicator portion 11 includes a constant vertical reference 13. The guidance device 10 includes graduated markings 14 arranged on a peripheral surface configured to indicate an angular rotation from a vertical reference point. In this embodiment, the graduated markings are arranged around a circumference of the indicator portion 11.

In this embodiment, the guidance device 10 is placed on the surgical instrument 15 shaft near a proximal end. In operation, the vertical reference 13 may be aligned with the bend of the surgical instrument distal end 16 and the indicator graduated markings (preferably the zero angle position). The attachment portion 12 may then be secured to the surgical instrument 15. The rotation of the instrument shaft will produce rotation of the indicator portion 11 and the instrument distal end 16. The vertical reference 13 will remain in the same vertical position, e.g., 12 o'clock position. Thereby, the graduated markings on the indicator portion will indicate the angular displacement, e.g., 0 degrees to 360 degrees, of the shaft and distal end 16 of the surgical instrument 15. In this embodiment, the distal end of the surgical instrument 15 includes a 16 vertical bend and the indicator portion reading 0 degrees at the vertical reference, a counter-clockwise rotation of the instrument shaft, e.g., 40 degrees, will produce a corresponding 40 degree rotation and the graduated mark 14 on the indicator 11 will read 40 degrees at the vertical reference 13.

Figure 2:
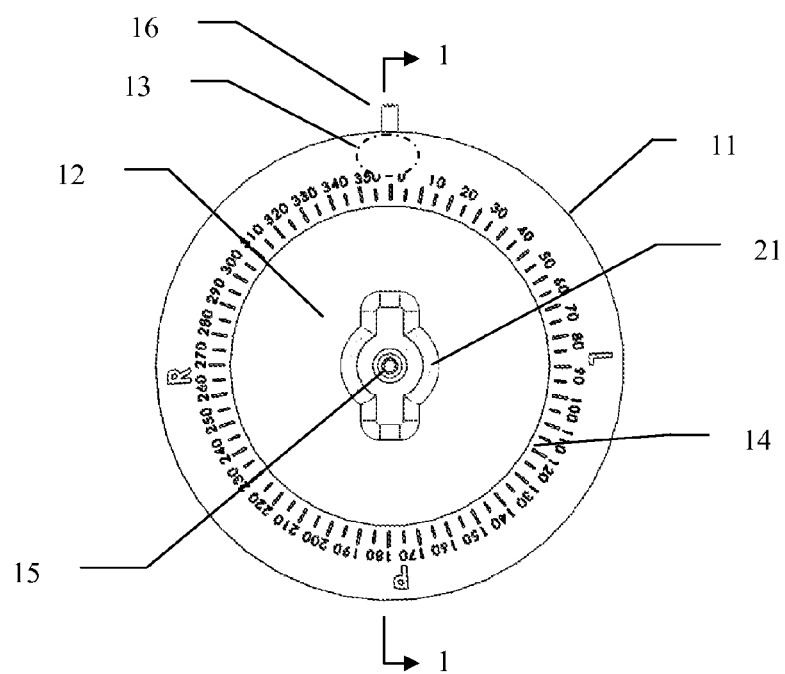
FIG. 2 is a front view of the guidance device in FIG. 1.
Figure 3:
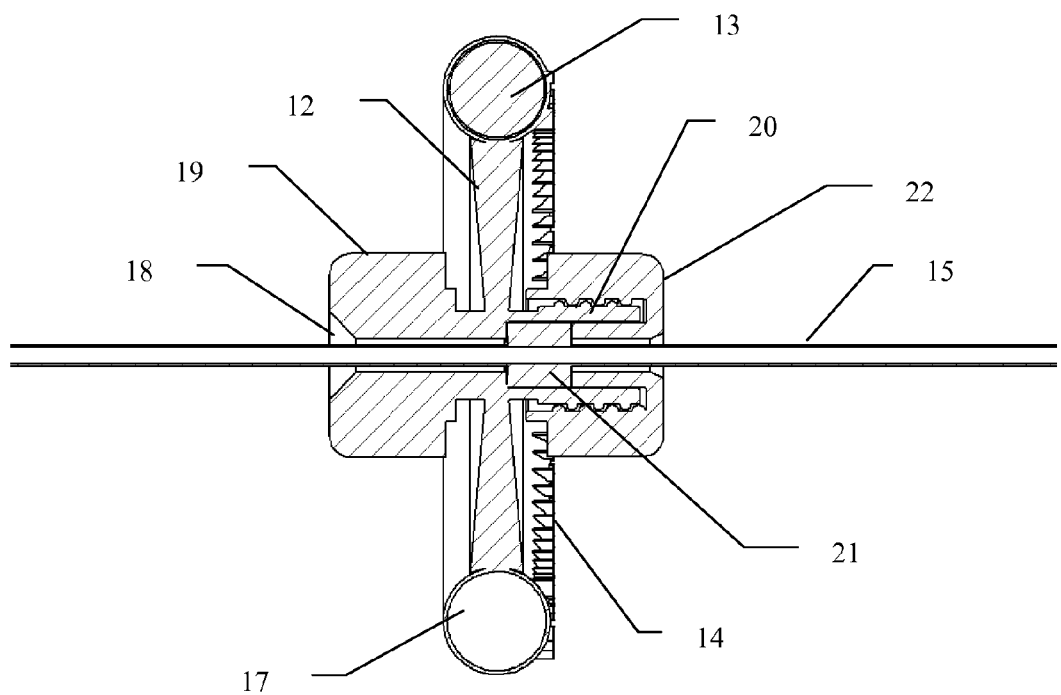
FIG. 3 is a cross sectional view of the guidance device in FIG. 1 taken across section 1-1.

As shown in FIGS. 1-3, indicator portion 11 includes a circular spirit level mounted in a coaxial orientation to the surgical instrument 15. In this embodiment, the spirit level is a clear tube incompletely filled with fluid 17 to leave a small gas bubble that will move to the highest section of the tube as the fluid is heavier than the gas upon rotation. The fluid in this embodiment includes an alcohol solution. The gas bubble in the indicator portion 11 is the vertical reference 13 as it will always be at the top (12 o'clock position) of the circular tube. The indicator portion 11 has raised graduated markings 14 including lines, numerals, and letters.

FIG. 2 shows line graduations every 5 degrees and numerals 0 to 360 degrees in 10 degree increments, however, any graduation may be used. Also shown in FIG. 2 are letters indicating rotation direction, A for anterior, P for posterior, R for right, L for left. Other letters indicating clockwise, counter-clockwise, or directions relative to patient anatomy or the type of surgical procedure could also be used.

Referring to FIG. 3, a securing portion 12 includes a cylindrical, plate-shaped structure with a concave outer edge matching the diameter of the tube of the indicator portion. A lumen 18 runs through the center of the securing portion 12 and is adapted to longitudinally accept the surgical instrument 15. Communicating with the hole on each side of the plate structure are hollow bosses 19 and 20 aligned coaxially with lumen 18. Boss 20 is threaded on the outer surface and has an inner diameter sized to accept a cylindrical seal 21, e.g., o-ring. Cap 22 is threaded on boss 20 and compresses the o-ring 21 to the surgical instrument 15 and thus prevents any longitudinal or rotational movement of the guidance device 10 independent of the surgical instrument 15. In this embodiment, the configuration of the boss 20, o-ring 21, and cap 22 is configured as Touhy Borst connection. Boss 19 is to provide gripping mechanism for the guidance device 10, useful when tightening or loosening cap 22, and has an outer shape similar to the cap. Other attachment mechanisms as know in the art may also be used.

Figure 4:
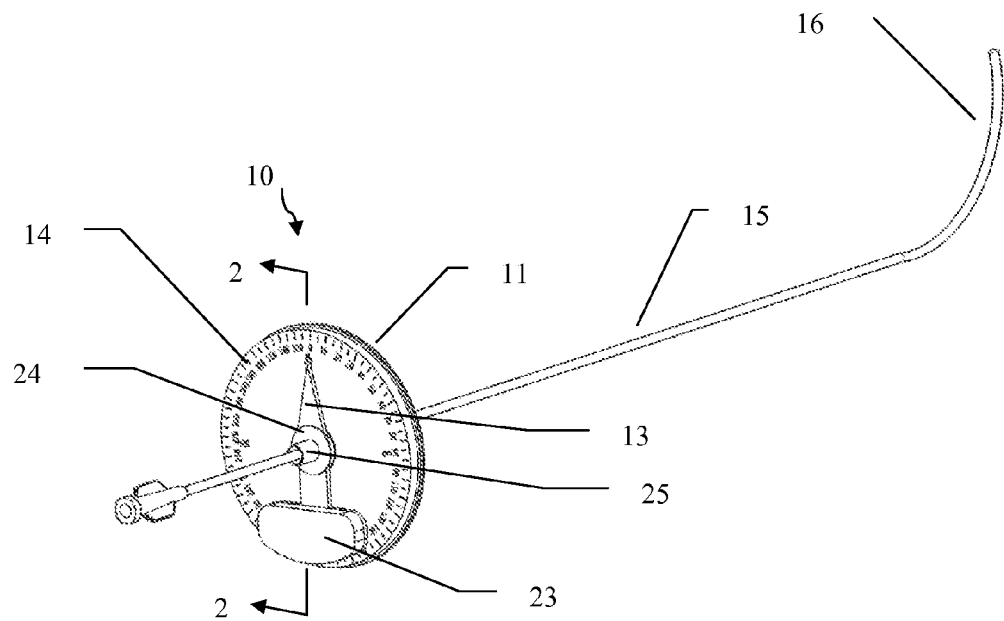
FIG. 4 a perspective view of the guidance device according to another embodiment.
Figure 5:
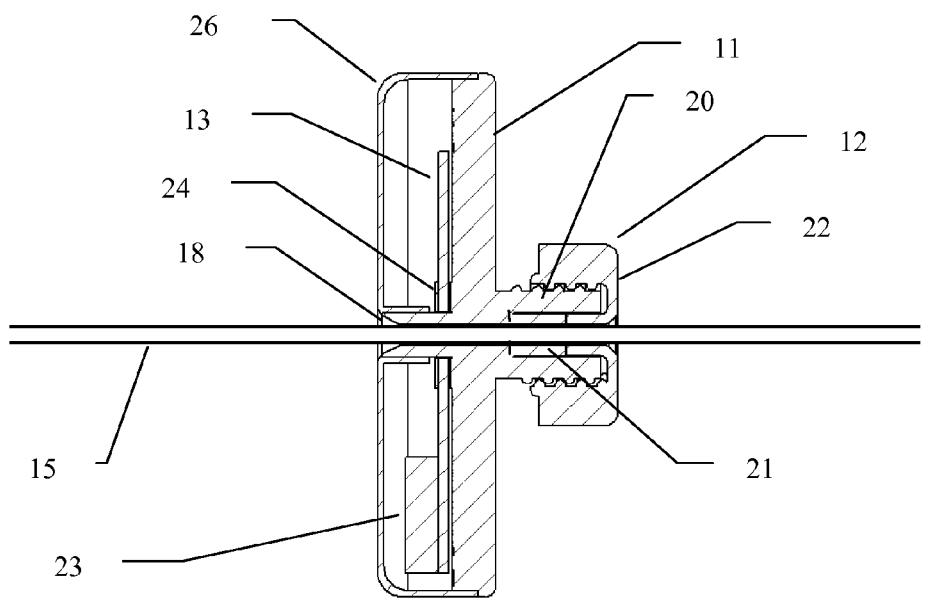
FIG. 5 is a cross sectional view of the guidance device in FIG. 4 taken across section 2-2.

FIG. 4 is a perspective view of the guidance device according to another embodiment. FIG. 5 is a cross sectional view of the guidance device in FIG. 4 taken across section 2-2.

Referring to FIGS. 4 and 5, the device 10 includes an indicator portion 11 having a cylindrical plate shaped structure with graduated markings 14 near an outer edge. The device includes a central lumen 18 sized to longitudinally accept the surgical instrument 15. A hollow boss 25 extends from a surface and supports a constant vertical reference. The constant vertical reference includes a thin sheet structure with a pointer 13 upper section extending near the graduated markings 14 and a counter-weight 23. The constant vertical reference is supported via a central hole sized to fit loosely over boss 25 and a washer 24. The counter-weight 23 includes a heavy mass attached and shaped with a wide bottom as compared to the pointer 13 creating a pendulum effect where the counter-weight 23 is hanging straight down due to gravity thereby ensuring the pointer 13 will always point straight up when the indicator portion 11 is rotated. The washer or washers 24 are loosely placed over boss 25 and on each side of the vertical reference 13 to prevent binding and friction. Lubricants may also be used.

Referring to FIG. 5, a protective clear housing 26 is optionally placed over vertical reference and face of indicator portion 11. Housing 26 is a plate shaped face spaced away from the vertical reference to allow free movement and contains a central, hollow boss extending toward the vertical reference 13 and sized to fit over boss 25. The clear housing 26 may include a magnification to enhance a user's ability to read the graduated markings 14. The sides of the housing 26 extend back to the outer diameter of the indicator portion and are attached by suitable mechanism, e.g., adhesive, welding, snap-fit and combinations of the same.

In this embodiment, a securing portion 12 is attached to the indicator portion on the opposite side in a Touhy Borst configuration. That is, it includes a threaded boss 20, a seal 21, e.g., o-ring, and cap 22 as discussed herein. The use and function of the above embodiment is exactly the same as the prior embodiment shown in FIGS. 1-3. Moreover, the device described with reference to FIGS. 4-5 may also be configured to work in an in-situ manner as described with reference to FIGS. 6-8. For example, the device may be configured with two-halves or in a slot configuration as described herein.

Figure 6:
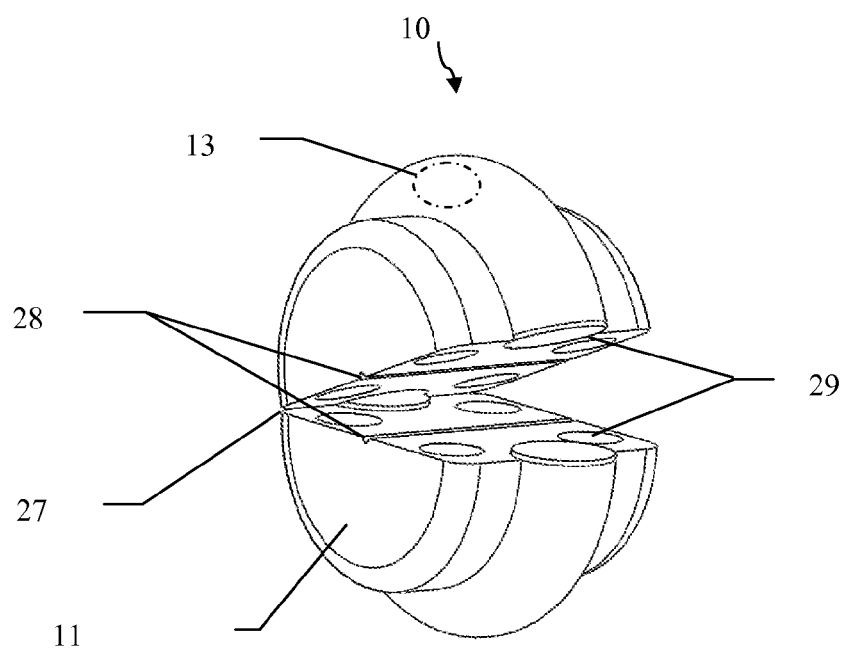
FIG. 6 is a perspective view of another embodiment of the invention.
Figure 7:
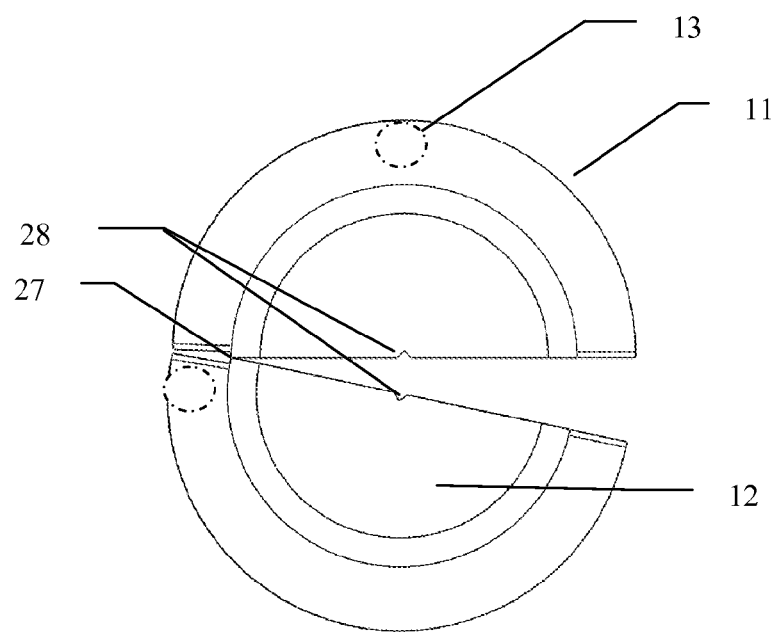
FIG. 7 is a side view of the guidance device in FIG. 6.

FIG. 6 is a perspective view of another embodiment of the invention. FIG. 7 is a side view of the guidance device in FIG. 6.

Referring to FIGS. 6 and 7, the guidance device 10 is configured to have an open position and a closed position. The Figures show the embodiment in an open position and ready to accept the surgical instrument 15 (not shown). This embodiment allows one to utilize the guidance device more readily, e.g., in an in-situ situation. The advantage of this embodiment is that it can be directly loaded onto the side of the surgical instrument 15 without having to thread the distal end of the instrument through the guidance device 10 before introduction into the body. This is particularly advantageous in situations where the surgical instrument is already inserted into the body as it prevents having to withdrawal the instrument to place the guidance device.

The guidance device 10 includes an indicator portion 11 having two semi-circular spirit levels mounted on securing portion 12. In this embodiment, a constant vertical reference 13 is contained in each of the two semi-circular spirit levels. Graduation marks (not shown) are placed on indicator portion 11.

Securing portion 12 includes two elastic semi-cylindrical structures with a slot in outer circumferential surface sized to accept and secure the indicator portion 11 with adhesive or other suitable mechanism. The ends of the indicator portion 11 are aligned with the flat inner surface of the securing portion 12. The two securing portion halves are connected to each other near the outer periphery by hinge 27 or other suitable mechanism. In a preferred embodiment, the hinge 27 is a 'living" hinge integral to securing portion 12. The flat internal surface of each half contains an aligned groove 28 sized to align and secure the surgical instrument 15 (not shown).

Opposing cylindrical magnets 29 are embedded below the surface in the flat internal surface of each securing portion half with poles positioned for attraction to each other. Alternately, cylindrical magnets are embedded in one half with the opposing half embedded with ferromagnetic metal cylinders. Other suitable releasable attachment mechanisms may also be used, e.g., adhesive, clip, and the like.

In operation, a surgical instrument 15 may be placed between the two semi-circular spirit levels and aligned with groove 28. When utilizing a surgical instrument with a bend 16 it is aligned with the vertical reference 13, graduation marks 14, and the two halves are pushed together and are secured in the closed position by the magnets. The elastic securing portion 12 is configured to compress around the surgical instrument shaft 15 and secure the device 10 to the surgical instrument 15. As the surgical instrument is rotated, the upper vertical reference 13 will align with the graduation marks to provide an angular measurement of rotation. Upon continued rotation of the surgical instrument the upper vertical reference 13 will reach the end of travel and will be replaced by the other vertical reference on the second semi-circular spirit level, thereby permitting in-situ loading of the guidance device to various surgical instruments.

Figure 8:
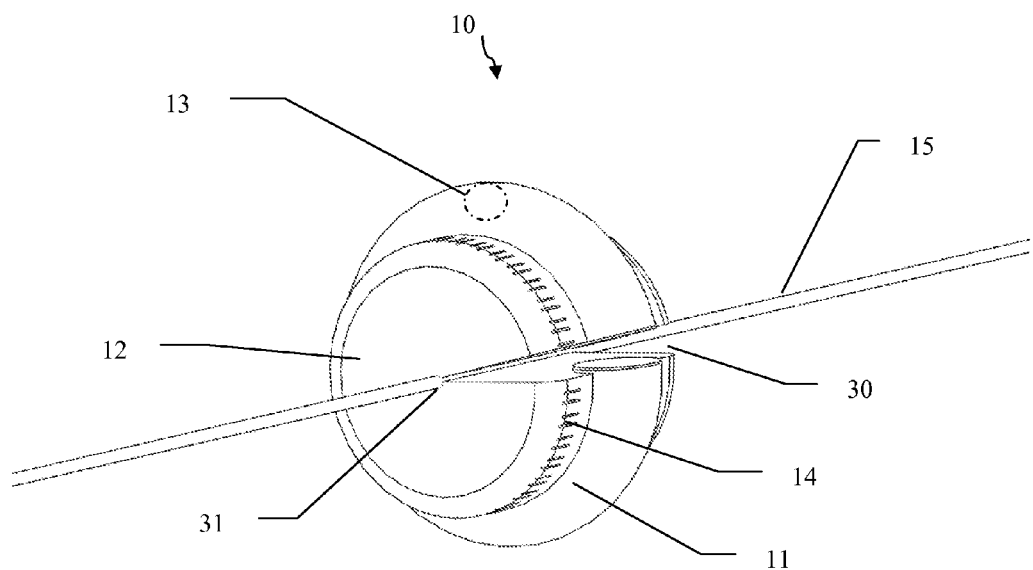
FIG. 8 is a perspective view of the guidance device according to another embodiment of the invention.

FIG. 8 shows another embodiment of the guidance device 10. Referring to FIG. 8, the guidance device 10 includes an indicator portion 11 having a semi-circular spirit level with an angular circumference of slightly less than 360 degrees. Securing portion 12 is a cylindrical shaped elastic structure with a slot in outer circumferential surface sized to accept and secure the indicator portion 11 with adhesive or other suitable mechanism. An angular slot 30 extends from the periphery of the securing section 12 to the interior and communicates with a lumen 31 extending through the securing portion 12 and co-axial to the outside diameter surface of the securing portion. The hole is configured to be slightly smaller than the surgical instrument 15 diameter. The slot 30 is positioned between the ends of the indicator portion 11 and is sized to allow side insertion of the surgical instrument into the lumen 31. Graduated markings 14 (shown without numerals) are placed on the outside diameter of the securing portion next to the indicator portion 11. To use, alignment of the vertical reference 13 and the surgical instrument distal end 16 and the graduated marks occurs as previously described. The surgical instrument 15 is then introduced into the slot 30 and pressed into the lumen 31. The elastic securing portion 12 compresses around the surgical instrument shaft and will secure the guidance device 10 to the surgical instrument 15. Rotation of the surgical instrument 15 is limited to less than 360 degrees total as the vertical reference 13 will reach the ends of the indicator portion 11. At this point the guidance device must be repositioned and rotated so that the vertical reference is in a central position between the two ends of the indicator portion 11.

Figure 9:
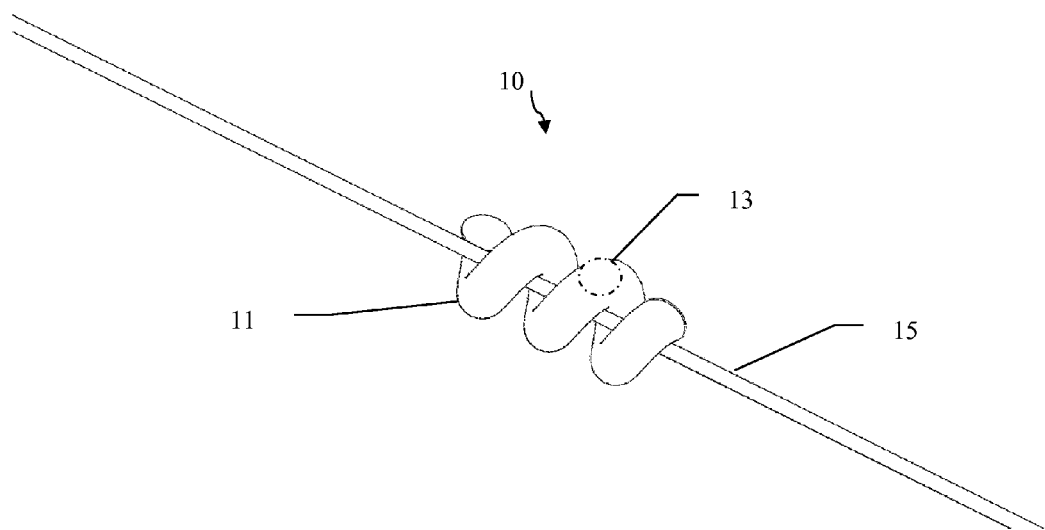
FIG. 9 is a perspective view of the guidance device according to another embodiment of the invention.

FIG. 9 shows another embodiment of the guidance device 10. Referring to FIG. 9, the guidance device 10 includes an indicator portion 11 configured as a helical shaped spirit level positioned co-axial with the surgical instrument 15. In this embodiment, the helical shaped spirit level is configured to rotate about 2.5 times around the surgical instrument 15 producing a total of about 900 degrees of rotation. Graduated markings (not shown) are placed on the outside surface of the indicator portion and numerals would read 0 to 360 degrees for each rotation of the helix. Directional markings could also be applied every 90 degrees as previously described. The inside diameter is sized to be slightly smaller than the surgical instrument diameter and the pitch of the helix is sized to allow threading of the guidance device 10 onto the instrument shaft 15. The smaller internal diameter of the helix will produce a slight bending of the surgical instrument when threaded over it, which will further produce a sufficient friction to secure guidance device 10 to surgical instrument 15. Other sealing mechanisms may be utilized, e.g., compressible material on the internal surface of the helix, to provide a releasable attachment of guidance device 10 to the surgical instrument 15.

Figure 10:
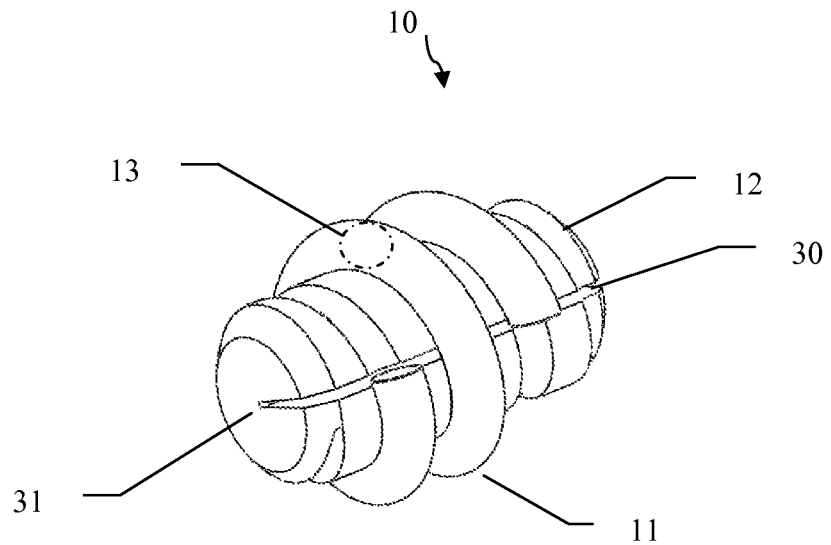
FIG. 10 is a perspective view of the guidance device according to another embodiment of the invention.

FIG. 10 shows an alternative embodiment of the guidance device 10. Indicator portion 11 consists of a helical spirit level extending for 2 full rotations. Securing portion 12 is a cylindrical shaped elastic structure with a helical groove extending for greater than 2 full rotations in outer circumferential surface and sized to allow the indicator portion 11 to be threaded onto it. An angular slot 30 extends from the periphery of the securing section 12 to the interior and communicates with the lumen 31 extending through the securing portion 12 and coaxial to the outside diameter surface of the securing portion. The hole is slightly smaller than the diameter of surgical instrument 15 (not shown). The slot is sized to allow side insertion of the surgical instrument 15 into lumen 31. Graduated markings (not shown) are placed on the outside diameter of the indicator portion 11. To use, securing portion and indicator portion are separated from each other and the securing portion is placed onto the instrument shaft first.

The surgical instrument 15 is then introduced into the slot 30 and pressed into the lumen 31. The helical indicator portion is threaded onto the surgical instrument shaft and then threaded onto the securing portion. Threading of the helical indicator portion compresses elastic securing portion 12 around the surgical instrument shaft and secures the guidance device 10 to the surgical instrument 15. Alignment of the vertical reference 13 and the surgical instrument distal end 16 and the graduated marks occurs as previously described.

The guidance device 10 described in the above embodiments provides an effective and disposable means to determine angular rotation of a surgical instrument. It can be used on nearly all existing surgical instruments without modification.

Figure 11:
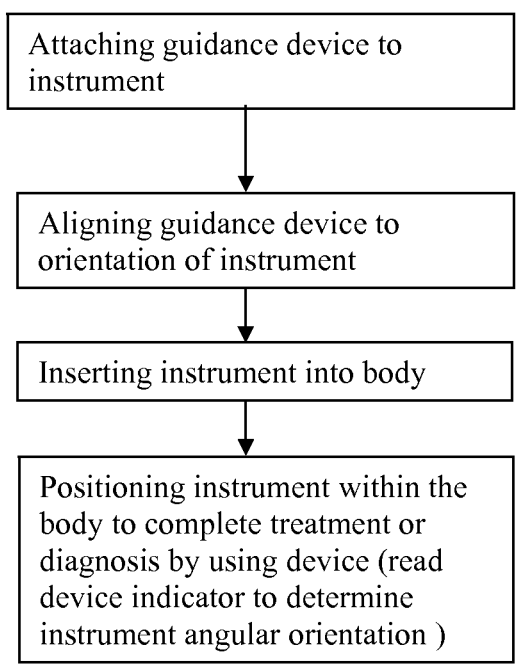
FIG. 11 is a flow chart for using the guidance device according to another embodiment of the invention.
Figure 12:
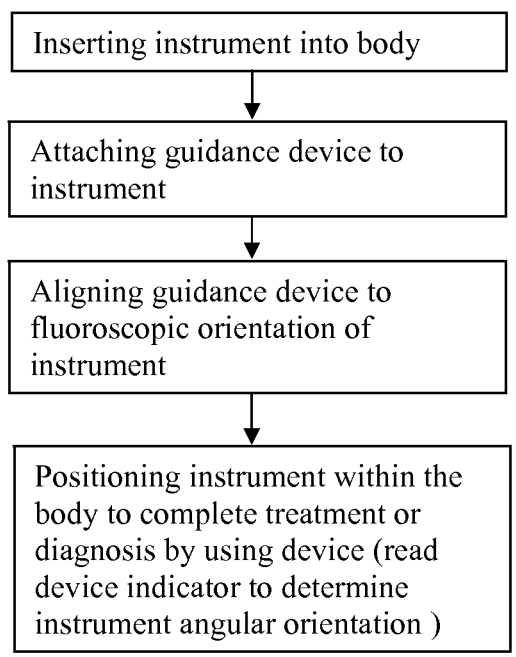
FIG. 12 is a flow chart for using the guidance device according to another embodiment of the invention.

FIGS. 11 and 12 illustrate flow charts for using the guidance device according to another embodiment of the invention. Referring to FIG. 11, the flow chart is directed towards using a guidance device when the guidance device is first attached to the shaft of the surgical instrument. That is, prior to insertion into the body the guidance device is attached to the surgical instrument. Next, the guidance device is aligned with the orientation of the surgical instrument, for example, the constant vertical reference and the "0" point of the indicator dial could be aligned to the "J" shape of a catheter as shown in FIG. 4. The surgical instrument is then inserted into the body so that the distal end of the instrument is within the body and the trailing end of the instrument and guidance device are located outside the body. Rotation of the trailing end of the instrument will produce rotation of the distal end of the instrument within the body. The guidance device will indicate to the user the degree of (angular) rotation the instrument has undergone and assist in accurately placing the instrument in position to complete the treatment or diagnosis.

Referring to FIG. 12, this flow chart is directed towards using the guidance device when the surgical instrument is already placed in the body. That is, the distal end is within the body and the proximal (trailing) end is outside the body. The guidance devices as show in FIGS. 6-10 may be used in this embodiment as these devices are configured to permit in-situ side-loading of the guidance device onto the trailing end of the instrument. After the guidance device has been attached to the surgical instrument it is then aligned with the fluoroscopic orientation of the surgical instrument. For example, the "J" shape of the distal end of a catheter is oriented so that the plane containing the curve is perpendicular to the x-ray source. Then the constant vertical reference and the "90" point of the indicator dial are aligned and the guidance device is tightly secured to the instrument. Rotation of the trailing end of the instrument will produce rotation of the distal end of the instrument within the body. The guidance device will indicate the degree of (angular) rotation the instrument has undergone and assist in accurately placing the instrument in position to complete the treatment or diagnosis.

The inventions and methods described herein can be viewed as a whole, or as a number of separate inventions that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. Thus, it is intended that the present invention cover all of the modifications and variations of this invention provided they come within the scope of the appended claims and their equivalents.

What is claimed is:

1. An angular rotation guidance apparatus configured for use with one or more surgical instruments, the apparatus comprising:
    an indicator comprising a plurality of markings arranged around a circumference portion of the indicator;
    a securing device comprising a hub arranged at a central portion of the indicator, the hub comprising a lumen extending through the central portion of the indicator, a boss portion and a cap configured to be arranged on the boss portion;
    an indicator configured to indicate to a user a degree of an angular rotational measurement about a longitudinal axis of the one or more surgical instruments, and
    wherein the hub is configured to secure a portion of the one or more surgical instruments to the indicator and configured to receive the surgical instrument through the lumen of the hub such that a portion of the surgical instrument can extend through the hub.

2. The apparatus of claim 1, wherein the plurality of markings comprise graduated markings.

3. The apparatus of claim 1, wherein the indicator comprises a bubble.

4. The apparatus of claim 1, wherein the indicator comprises a pointer and a counter weight.

5. The apparatus of claim 1, wherein the indicator is configured to provide 360 degrees of angular rotational measurement.

6. The apparatus of claim 1, wherein the securing device comprises a hub configured to receive a portion of the surgical instrument.

7. The apparatus of claim 1, wherein the one or more surgical instruments is selected from a group consisting of a guidewire and a catheter.

8. An angular rotation guidance apparatus for use with a surgical instrument, the apparatus comprising:
    an indicator comprising a plurality of markings arranged around a circumference of the indicator and a constant vertical reference; and
    a hub arranged at a central portion of the indicator, the hub comprising a lumen extending through the central portion of the indicator, a boss portion and a cap configured to be arranged on the boss portion;
    wherein the vertical reference and the plurality of markings are configured to provide to a user a degree of an angular rotational measurement about a longitudinal axis of the surgical instrument, and
    wherein the hub is configured to secure a portion of the surgical instrument to the indicator and configured to receive the surgical instrument through the lumen of the hub such that a portion of the surgical instrument can extend through the hub.

9. The apparatus of claim 8, wherein the vertical reference comprises a bubble.

10. The apparatus of claim 8, wherein the vertical reference comprises a pointer and a counter weight.

11. The apparatus of claim 9, wherein the bubble is a gas bubble in a sealed fluid chamber.

12. The apparatus of claim 11, wherein the sealed fluid chamber comprises a fluid composed of an alcohol.

13. The apparatus of claim 11, wherein the sealed fluid chamber comprises a fluorescent fluid.

14. The apparatus of claim 8, wherein the plurality of markings comprise graduated markings arranged around a circumference of the indicator.

15. The apparatus of claim 14, wherein the graduated markings range from 0 degrees to 360 degrees.

16. The apparatus of claim 14, further comprising a seal arranged in a portion of the hub.

17. The apparatus of claim 8, wherein the indicator is configured as a handle or incorporated into the surgical device as a handle.

18. A method of using a guidance device to provide an angular orientation of a distal end of a surgical instrument, the method comprising the steps of:
    attaching a helically shaped guidance device around a longitudinal axis, the surgical instrument comprising a proximal end portion and a distal end portion after;
    aligning the guidance device and an indicator to a specific orientation of the surgical instrument; and
    measuring a degree of rotation about a longitudinal axis of the distal end portion of the surgical device with the indicator.

19. The method of claim 18, wherein the surgical device is selected from the group consisting of a catheter, guidewire, needle, forcep, biotome, endoscope, laproscope, and trocar.

20. A kit, comprising:
    a surgical instrument;
    an angular rotation guidance apparatus for use with a surgical instrument, comprising:
        an indicator comprising a plurality of markings arranged around a circumference of the indicator and a vertical reference;
        a securing device comprising a hub coupled to the indicator at a central portion of the indicator, the hub comprising a lumen extending through the central portion of the indicator, wherein the indicator is configured to provide 360 degrees of angular rotational measurement about a longitudinal axis of the surgical instrument; and
instructions for use.

* * * * *